United States Patent [19]

Denzel et al.

[11] 4,066,645
[45] Jan. 3, 1978

[54] DERIVATIVES OF PYRAZOLO [1,5-A]PYRIDO[3,4-E]PYRIMIDINE

[75] Inventors: Theodor Denzel, Regensburg; Hans Hoehn, Tegernheim, both of Germany

[73] Assignee: E. R. Squibb & Sons, Inc., Princeton, N.J.

[21] Appl. No.: 794,769

[22] Filed: May 9, 1977

[51] Int. Cl.² ............ C07D 471/04; A61K 31/415
[52] U.S. Cl. ............ 260/256.4 F; 424/251; 260/256.5 R
[58] Field of Search ............ 260/256.4 F, 256.5 R

[56] References Cited

U.S. PATENT DOCUMENTS

| | | | |
|---|---|---|---|
| 3,045,015 | 7/1962 | Miller, et al. | 260/256.4 F |
| 4,002,755 | 1/1977 | Yamamoto, et al. | 260/256.4 F |

*Primary Examiner*—Paul M. Coughlan, Jr.
*Assistant Examiner*—James H. Turnipseed
*Attorney, Agent, or Firm*—Lawrence S. Levinson; Merle J. Smith

[57] ABSTRACT

New derivatives of pyrazolo[1,5-a]pyrido[3,4-e]pyrimidine have the general formulas

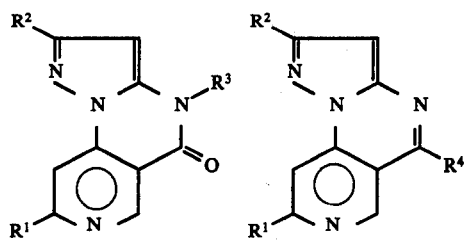

The compounds are useful as anti-inflammatory agents.

23 Claims, No Drawings

DERIVATIVES OF PYRAZOLO [1,5-A]PYRIDO[3,4-E]PYRIMIDINE

SUMMARY OF THE INVENTION

This invention relates to a series of new pyrazolo[1,5-a]-pyrido[3,4-e]pyrimidine compounds. These new compounds have the general formulas

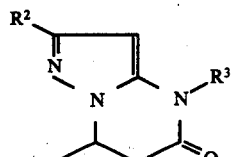
(I)

and

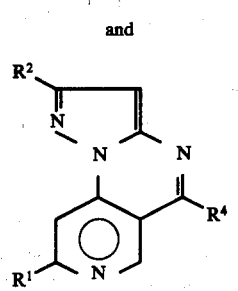
(II)

The symbols have the following meanings:

$R^1$ is hydrogen, halogen, hydroxy, lower alkylthio or lower alkoxy.

$R^2$ and $R^3$ each is hydrogen or lower alkyl.

$R^4$ is lower alkoxy, lower alkylthio, amino, lower alkylamino or di(lower alkyl)amino.

Preferred embodiments are those compounds wherein $R^1$ is hydrogen, halogen, especially chlorine, hydroxy or lower alkylthio, especially methylthio; $R^2$ is hydrogen or lower alkyl, especially the latter and most especially methyl; $R^3$ is hydrogen or lower alkyl, especially hydrogen or methyl; and $R^4$ is halogen, especially chlorine, lower alkoxy, especially ethoxy, lower alkylamino, especially butylamino or di(lower alkyl)amino, especially diethylamino. Preferably at least one, and especially two, of the substituents $R^1$, $R^2$, $R^3$ and $R^4$ is other than hydrogen. Within the group of compounds which have the formula I, there are particularly preferred those compounds wherein $R^1$ is hydrogen, halogen, especially chlorine, hydroxy or lower alkylthio, especially methylthio; $R^2$ is lower alkyl, especially methyl; and $R^3$ is hydrogen or lower alkyl, especially hydrogen or methyl. Particularly preferred compounds of formula II are those wherein $R^1$ is hydrogen or halogen, especially chlorine; $R^2$ is lower alkyl especially methyl; and $R^4$ is the same as described above.

REFERENCE TO RELATED APPLICATIONS

Reference is made to our related applications Ser. Nos. 783,252 and 783,253, both filed Mar. 31, 1977.

DETAILED DESCRIPTION OF THE INVENTION

The lower alkyl groups are the aliphatic hydrocarbon groups, both straight and branched chain, having up to seven carbon atoms. The $C_1$-$C_4$ and especially the $C_1$-$C_2$ groups are preferred. The lower alkoxy and lower alkylthio groups are of the same type with the same preferences. Illustrative are the following: methyl, ethyl, propyl, isopropyl, butyl, isobutyl, t-butyl, amyl, methoxy, ethoxy, propoxy, isopropoxy, butoxy, t-butoxy, methylthio, ethylthio, propylthio, isopropylthio, butylthio and the like.

The amino substituents represented by $R^4$ are those having the structure

wherein $R^5$ and $R^6$ each represents hydrogen or a lower alkyl of the type described above. These include for example, amino, lower alkylamino groups like methylamino, ethylamino, propylamino, isopropylamino, butylamino (which is especially preferred), dimethylamino, diethylamino (which is also especially preferred), methylethylamino, dipropylamino, dibutylamino and the like.

All four common halogens are contemplated, but chlorine and bromine, especially the first, are preferred.

The new compounds are produced by the following series of reactions from the first member of the series which has the formula

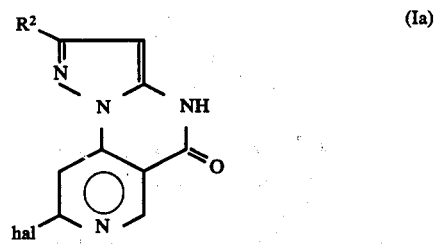
(Ia)

wherein hal represents halogen, preferably chlorine (i.e., $R^1$ is halogen and $R^3$ is hydrogen).

Catalytic hydrogenation of the compound of formula Ia, e.g., in the presence of palladium on charcoal, Raney nickel or the like, yields a product of the formula

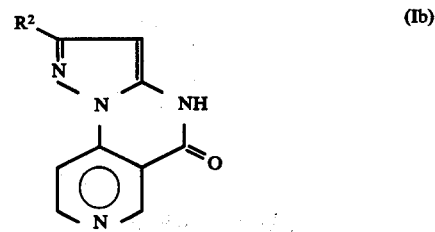
(Ib)

(i.e., $R^1$ and $R^3$ each is hydrogen).

By treating a compound of formula Ia with a strong acid like concentrated sulfuric acid at an elevated temperature of about 150° C. yields a product of the formula

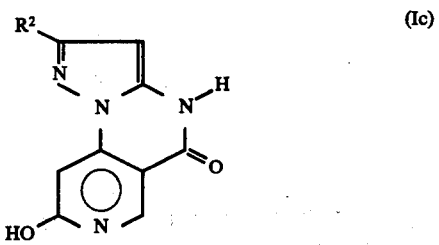
(Ic)

(i.e., $R^1$ is hydroxy and $R^3$ is hydrogen.)
Compounds of the formula

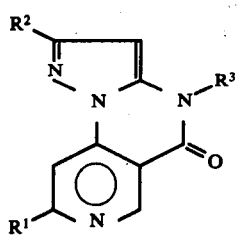 (Id)

wherein $R^3$ is other than hydrogen are now obtained by treatment of a compound of formula Ia, Ib or Ic with an appropriate alkyl halide in the presence of a base like potassium carbonate in a solvent like dimethylformamide or the like.

Compounds of the formula

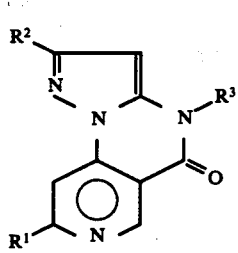 (Ie)

wherein $R^1$ is lower alkoxy or lower alkylthio are obtained by treatment of a compound of formula Id ($R^1$ is halo) with the appropriate alkali metal lower alkoxide or alkali metal mercaptide of the formula lower alkyl-X-Me, wherein X is oxygen or sulfur and Me is alkali metal.

Compounds of the formula

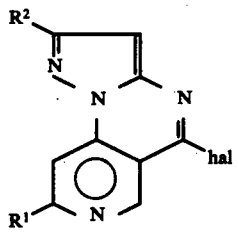 (IIa)

wherein $R^4$ is halogen are prepared by the reaction of a compound of formula Ia, Ib or Ic with a halogenating agent like phosphorus oxychloride.

Compounds of the formula

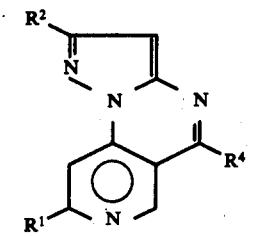 (IIb)

wherein $R^4$ is lower alkoxy, lower alkylthio or the amino group

are prepared by reaction of a compound of formula IIa with an alkali metal lower alkoxide, alkali metal lower alkylmercaptide or amine of the formula

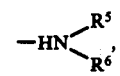

respectively.

The starting material of formula Ia is produced by reacting a 4,6-dihalopyridine-3-carboxylic acid, alkyl ester [produced according to the procedure of G. Lhommet and P. Maitte, C.R. Acad. Sci. Ser. C 275, 1317 (1972)] of the formula

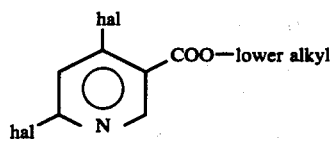 (III)

wherein hal represents halogen, preferably chlorine or bromine, with hydrazine, forming a compound of the formula

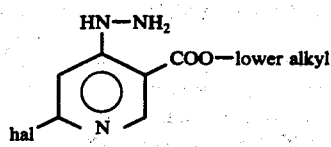 (IV)

This compound is reacted with an aminocrotonic acid nitrile of the formula

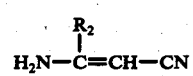 (V)

to form a product of the formula $$HN-NH-\overset{R^2}{C}=CH-CN$$ (VI)

[structure with COOalkyl and hal substituents on pyridine]

Treatment of the product of formula VI with a Lewis catalyst like zinc chloride, boron trifluoride or the like in a solvent like acetic acid yields the product of formula Ia.

Additional experimental details are found in the examples which follow.

The new compounds of this invention have antiinflammatory properties and are useful, for example, to reduce local inflammatory conditions such as those of an edematous nature or resulting from proliferation of connective tissue in various mammalian species such as rats, dogs and the like when given orally in dosages of about 5 to 175 mg/kg/day, preferably 10 to 50 mg/kg/day, in single or 2 to 4 divided doses, as indicated by the carageenan edema assay or delayed hypersensitivity reaction in rats. The active substance can be utilized in compositions such as tablets, capsules, solutions or suspensions containing up to about 500 mg. per unit of dosage of a compound or mixture of compounds of formulas I or II. They are compounded in conventional manner with a physiologically acceptable vehicle or carrier, excipient, binder, preservative, stabilizer, flavor, etc. as called for by accepted pharmaceutical practice. Topical preparations containing about 0.05 to 5 percent by weight of active substance in a lotion or cream can also be used.

The following examples are illustrative of the invention. Additional members can be made according to these prototypes by appropriate substitution of the starting materials. All temperatures are in degrees celsius.

EXAMPLE 1

8-Chloro-2-methylpyrazolo[1,5-a]pyrido[3,4-e]pyrimidin5(4H)-one a. 6-Chloro-4-hydrazino-3-pyridinecarboxylic acid, methyl ester 205 g. of 4,6-dichloro-3-pyridinecarboxylic acid, methyl ester (1 mol.) are dissolved in 1 liter of methanol. The solution is cooled to 0° and 100 g. of hydrazine hydrate are dropped in with stirring. The solution is kept at 0° for 12 hours. The precipitated 6-chloro-4-hydrazino-3-pyridinecarboxylic acid, methyl ester is filtered off and recrystallized from methanol, yield: 175 g. (87%); m.p. 163.3°.

b. 8-Chloro-2-methylpyrazolo[1,5-a]pyrido[3,4-e]pyrimidin5(4H)-one 3 g. of 6-chloro-4-hydrazino-3-pyridinecarboxylic acid, methyl ester and 2.4 g. of 3-aminocrotonic acid nitrile are refluxed in 10 ml. of methanol for 72 hours. After this time, 8-chloro-2-methylpyrazolo[1,5-a]pyrido[3,4-e]-pyrimidin-5(4H)-one is filtered off, yield: 2.5 g. (73%); m.p. > 300°.

EXAMPLE 2

2-Methylpyrazolo[1,5-a]pyrido[3,4-e]pyrimidin-5(4H)-one 2.3 g. of 8-chloro-2-methylpyrazolo[1,5-a]pyrido[3,4-e]pyrimidin-5(4H)-one are hydrogenated in 50 ml. of dimethylformamide in the presence of 10% palladium on charcoal and 2 g. of triethylamine at 80° and 3 atmospheres hydrogen pressure. When the hydrogen absorption ceases, the solution is heated to reflux temperature and then filtered. After addition of 20 ml. of water, 2-methylpyrazolo[1,5-a]pyrido[3,4-e]pyrimidin-5(4H)-one crystallizes, yield: 1.8 g. (90%); m.p. > 300°.

EXAMPLE 3

2,4-Dimethylpyrazolo[1,5-a]pyrido[3,4-e]pyrimidin-5(4H)-one 2 g. of 2-methylpyrazolo[1,5-a]pyrido[3,4-e]pyrimidin5(4H)-one are treated with 2 g. of methyl iodide in 20 ml. of dimethylformamide in the presence of 2 g. of potassium carbonate at 70° with stirring for 12 hours. The mixture is cooled to room temperature, 20 ml. of water are added and the precipitated 2,4-dimethylpyrazolo[1,5-a]pyrido[3,4-e]pyrimidin-5(4H)-one is filtered off, yield: 1.5 g. (70%); m.p. > 300° (DMF).

EXAMPLE 4

2,4-Dimethyl-8-chloropyrazolo[1,5-a]pyrido[3,4-e]pyrimidin5(4H)-one

When in Example 3 the 2-methylpyrazolo[1,5-a]pyrido[3,4-e]pyrimidin-5(4H)-one is replaced by the 8-chloro-2-methylpyrazolo[1,5-a]pyrido[3,4-e]pyrimidin-5(4H)-one pf Example 1b, 2,4-dimethyl-8-chloropyrazolo[1,5-a]pyrido[3,4-e]pyrimidin-5(4H)-one is obtained, yield: 73%; m.p. 253.8° (DMF).

EXAMPLE 5

2,4-Dimethyl-8-methylthiopyrazolo[1,5-a]pyrido[3,4-e]-pyrimidin-5(4H)-one 2.5 g. of 2,4-dimethyl-8-chloropyrazolo[1,5-a]pyrido[3,4-e]pyrimidin-5(4H)-one are treated with 1.5 g. of sodium methylmercaptide in 20 ml. of dimethylformamide at 100° for 12 hours. The mixture is cooled to room temperature and 10 ml. of water are added. Crystalline 2,4-dimethyl-8-methylthiopyrazolo[1,5-a]pyrido[3,4-e]pyrimidin-5(4H)-one is filtered off, yield: 1.6 g. (62%); m.p. > 300° (DMF).

EXAMPLE 6

2,4-Dimethyl-8-ethoxypyrazolo[1,5-a]pyrido[3,4-e]pyrimidin5(4H)-one

By substituting sodium ethoxide in ethanol for the sodium methylmercaptide in DMF in the procedure of Example 5, 2,4-dimethyl-8-ethoxypyrazolo[1,5-a]pyrido[3,4-e]pyrimidin-5(4H)-one is obtained.

EXAMPLE 7

8-Hydroxy-2-methylpyrazolo[1,5-a]pyrido[3,4-e]pyrimidin5(4H)-one 2.3 g. of 8-chloro-2-methylpyrazolo[1,5-a]pyrido[3,4-e]pyrimidin-5(4H)-one of Example 1b are refluxed with 1 g. of zinc chloride in 20 ml. of acetic acid for 100 hours. The mixture is cooled to room temperature, diluted with 10 ml. of water and the precipitated 8-hydroxy-2-methylpyrazolo[1,5-a]pyrido[3,4-e]pyrimidin5(4H)-one is filtered off, yield: 1.7 g. (81%); m.p. > 300° (DMF).

EXAMPLE 8

5-Ethoxy-2-methylpyrazolo[1,5-a]pyrido[3,4-e]pyrimidine a. 5-Chloro-2-methylpyrazolo[1,5-a]pyrido[3,4-e]pyrimidine 200 g. of 2-methylpyrazolo[1,5-a]pyrido[3,4-e]-pyrimidin-5(4H)-one of Example 1c are refluxed with 800 ml. of phosphorus oxychloride overnight. The excess phosphorus oxychloride is removed in vacuo and the oily residue decomposed by pouring on ice. The acidic aqueous solution is made alkaline with sodium hydroxide. The precipitated 5-chloro-2-methylpyrazolo[1,5-a]pyrido[3,4-e]pyrimidine is filtered off, yield: 143 g. (66%); m.p. 169.8° (ethyl acetate).

b. 5-Ethoxy-2-methylpyrazolo[1,5-a]pyrido[3,4-e]pyrimidine 2.2 g. of 5-chloro-2-methylpyrazolo[1,5-a]pyrido[3,4-e]pyrimidine are added to a solution of 0.5 g. of sodium in 30 ml. of ethanol. The solution is refluxed with stirring for 12 hours. 10 ml. of water are added and the crystalline 5-ethoxy-2-methylpyrazolo[1,5-a]pyrido[3,4-e]pyrimidine is filtered off, yield: 1.4 g. (61%); m.p. 156.2° (methanol).

EXAMPLE 9

8-Chloro-5-ethoxy-2-methylpyrazolo[1,5-a]pyrido[3,4-e]pyrimidine a. 5,8-Dichloro-2-methylpyrazolo[1,5-a]pyrido[3,4-e]pyrimidine 23.5 g. of 8-chloro-2-methylpyrazolo[1,5-a]pyrido[3,4-e]pyrimidin-5(4H)-one of Example 1b are refluxed in 100 ml. of phosphorus oxychloride for 12 hours. The excess phosphorus oxychloride is distilled off in vacuo and the oily residue is poured on ice. After standing for 1 hour, 5,8-dichloro2-methylpyrazolo[1,5-a]pyrido[3,4-e]pyrimidine is filtered off, yield: 17 g. (67%); m.p. 203.4° (ethyl acetate).

b. 8-Chloro-5-ethoxy-2-methylpyrazolo[1,5-a]pyrido[3,4-e]pyrimidine 2.5 g. of 5,8-dichloro-2-methylpyrazolo[1,5-a]pyrido[3,4-e]pyrimidine are added to a solution of 0.3 g. sodium in 20 ml. of ethanol. The mixture is stirred at 60° for 1 hour. After addition of 10 ml. of water, 8-chloro-5-ethoxy-2-methylpyrazolo[1,5-a]pyrido[3,4-e]pyrimidine precipitates and is filtered off, yield: 1.8 g. (68%); m.p. 175.6° (ethyl acetate).

EXAMPLE 10

N-Butyl-2-methylpyrazolo[1,5-a]pyrido[3,4-e]pyrimidin-5-amine 2.2 g. of 5-chloro-2-methylpyrazolo[1,5-a]pyrido[3,4-e]pyrimidine of Example 18 are refluxed in 10 ml. of n-butylamine for 12 hours. The excess amine is evaporated and the residue treated with 10 ml. of water. N-Butyl-2-methylpyrazolo[1,5-a]pyrido[3,4-e]pyrimidin-5-amine is filtered off, yield: 2 g. (80%); m.p. 116.1° (methanol).

EXAMPLE 11

N,N-diethyl-2-methylpyrazolo[1,5-a]pyrido[3,4-e]pyrimidin-5-amine

When the Example 10 n-butylamine is replaced by N,N-diethylamine, N,N-diethyl-2-methylpyrazolo[1,5-a]pyrido[3,4-e]-pyrimidin-5-amine is obtained, yield: 83% m.p. 118.1° (methanol).

EXAMPLE 12

2-Methylpyrazolo[1,5-a]pyrido[3,4-e]pyrimidin-5-amine

When in Example 10 n-butylamine is replaced by concentrated ammonia, 2-methylpyrazolo[1,5-a]pyrido[3,4-e]pyrimidin-5-amine is obtained.

EXAMPLE 13

5-Methylthio-2-methylpyrazolo[1,5-pyrido[3,4-e]pyrimidine

When in Example 8b the sodium in ethanol is replaced by sodium methylmercaptide in dimethylformamide, 5-methylthio-2-methylpyrazolo[1,5-a]pyrido[3,4-e]pyrimidine is obtained.

What is claimed is:

1. A compound having the formula

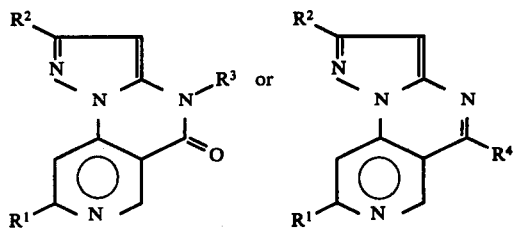

wherein
$R^1$ is hydrogen, halogen, hydroxy, lower alkylthio or lower alkoxy;
$R^2$ and $R^3$ each is hydrogen or lower alkyl; and
$R^4$ is lower alkoxy, lower alkylthio, amino, lower alkylamino or di(lower alkyl)amino.

2. A compound as in claim 1 wherein $R^1$ is hydrogen, halogen, hydroxy or lower alkylthio; $R^2$ and $R^3$ each is hydrogen or lower alkyl and $R^4$ is halogen, lower alkoxy, lower alkylamino or di(lower alkyl) amino.

3. A compound having the formula

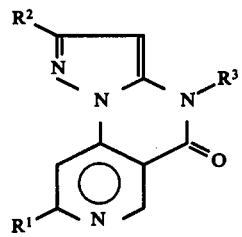

wherein
$R^1$ is hydrogen, halogen, hydroxy or lower alkylthio;
$R^2$ is lower alkyl; and
$R^3$ is hydrogen or lower alkyl.

4. A compound having the formula

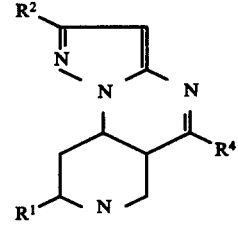

wherein
$R^1$ is hydrogen or halogen;
$R^2$ is lower alkyl; and
$R^4$ is lower alkoxy, lower alkylthio, amino, lower alkylamino or di(lower)alkyl amino.

5. A compound as in claim 3 wherein $R^1$ is halogen.
6. A compound as in claim 4 wherein $R^1$ is halogen.
7. A compound as in claim 3 wherein $R^2$ is lower alkyl.
8. A compound as in claim 4 wherein $R^2$ is lower alkyl.
9. A compound as in claim 3 wherein $R^3$ is hydrogen.
10. A compound as in claim 7 wherein $R^3$ is lower alkyl.
11. A compound as in claim 4 wherein $R^4$ is lower alkoxy.
12. A compound as in claim 4 wherein $R^4$ is lower alkylamino.

13. A compound as in claim 4 wherein $R^4$ is di(lower alkyl)amino.

14. A compound as in claim 3 wherein $R^1$ and $R^3$ each is hydrogen and $R^2$ is methyl.

15. A compound as in claim 3 wherein $R^1$ is chlorine, $R^2$ is methyl and $R^3$ is hydrogen.

16. A compound as in claim 3 wherein $R^1$ is chlorine and $R^2$ and $R^3$ each is methyl.

17. A compound as in claim 4 wherein $R^1$ and $R^4$ each is chlorine and $R^2$ is methyl.

18. A compound as in claim 4 wherein $R^1$ is hydrogen, $R^2$ is methyl and $R^4$ is chlorine.

19. A compound as in claim 4 wherein $R^1$ is chlorine, $R^2$ is methyl and $R^4$ is ethoxy.

20. A compound as in claim 3 wherein $R^1$ is methylthio and $R^2$ and $R^3$ each is methyl.

21. A compound as in claim 4 wherein $R^1$ is hydrogen, $R^2$ is methyl and $R^4$ is ethoxy.

22. A compound as in claim 4 wherein $R^1$ is hydrogen, $R^2$ is methyl and $R^4$ is butylamino.

23. A compound as in claim 4 wherein $R^1$ is hydrogen, $R^2$ is methyl and $R^4$ is diethylamino.

* * * * *